US008173179B1

(12) United States Patent
Abbas et al.

(10) Patent No.: US 8,173,179 B1
(45) Date of Patent: May 8, 2012

(54) GRANULAR BIOPLASTIC BIOCONTROL COMPOSITION

(75) Inventors: Hamed K. Abbas, Greenville, MS (US); Cesare Accinelli, Bologna (IT); Robert M. Zablotowicz, Cleveland, MS (US); Maria L. Sacca, Rome (IT); Jeff Wilkinson, Beaumont, TX (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 201 days.

(21) Appl. No.: 12/703,257

(22) Filed: Feb. 10, 2010

Related U.S. Application Data

(60) Provisional application No. 61/151,409, filed on Feb. 10, 2009.

(51) Int. Cl.
*A01N 65/00* (2009.01)

(52) U.S. Cl. ........................................................ 424/725

(58) Field of Classification Search ........................ None
See application file for complete search history.

(56) References Cited

FOREIGN PATENT DOCUMENTS

WO WO 2006/076245 * 7/2006

* cited by examiner

*Primary Examiner* — Michael Meller
(74) *Attorney, Agent, or Firm* — John D. Fado; Evelyn M. Rabin

(57) ABSTRACT

Previous research demonstrated that aflatoxin contamination in corn is reduced by field application of wheat grains pre-inoculated with the non-aflatoxigenic *Aspergillus flavus* strain NRRL 30797. To facilitate field applications of the biocontrol isolate, a series of laboratory studies were conducted on the reliability and efficiency of replacing wheat grains with the novel bioplastic formulation Mater-Bi® to serve as a carrier matrix to formulate this fungus. Mater-Bi® granules were inoculated with a conidial suspension of NRRL 30797 to achieve a final cell density of ~log 7 conidia/granule. Incubation of 20-g soil samples receiving a single Mater-Bi® granule for 60-days resulted in log 4.2 to 5.3 propagules of *A. flavus*/g soil for microbiologically active and sterilized soil, respectively. Increasing the number of granules had no effect on the degree of soil colonization by the biocontrol fungus. In addition to the maintenance of rapid vegetative growth and colonization of soil samples, the bioplastic formulation was highly stable, indicating that Mater-Bi® is a suitable substitute for biocontrol applications of *A. flavus* NRRL 30797.

2 Claims, 12 Drawing Sheets

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 1

acggatcact tagccagcac                                                   20


<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2

ctaccagggg agttgagatc c                                                 21


<210> SEQ ID NO 3
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 3

gccttgacat ggaaaccatc                                                   20


<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4

ccaagatggc ctgctcttta                                                   20


<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 5
```

-continued gccttgcaaa cacactttca 20

<210> SEQ ID NO 6
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 6
agttgttgaa cgccccagt 19

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
cgactgttgg ccttttcatt 20

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 8
atagcgaggt tccagcgtaa 20

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
cgagttgtgc cagttcaaaa 20

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 10
aatcctcgcc caccatacta 20

<210> SEQ ID NO 11
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 11
tccgtaggtg aacctgcgg 19

<210> SEQ ID NO 12
<211> LENGTH: 19
<212> TYPE: DNA
<213> ORGANISM: Artificial Sequence -continued

```
<220> FEATURE:
<223> OTHER INFORMATION: Chemically Synthesized

<400> SEQUENCE: 12

ggtccgtgtt tcaagacgg                                                19


<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 13

aagcagatca tcccagtgat                                               20


<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 14

cgagttgtgc cagttcaaaa                                               20


<210> SEQ ID NO 15
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 15

gctggtacaa tttggctgtc                                               20


<210> SEQ ID NO 16
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 16

cgcctccgac ttgacttctg                                               20
```

GRANULAR BIOPLASTIC BIOCONTROL COMPOSITION

This application claims the benefit of U.S. Provisional Application No. 61/151,409 filed Feb. 10, 2009, which is incorporated herein by reference in its entirety.

BACKGROUND OF THE INVENTION

1. Field of the Invention

This invention relates to a novel biocontrol formulation for the prevention of contamination of plants by toxins produced by fungi, i.e., toxigenic *Aspergillus* spp. and the control of seedling and root diseases. The novel biocontrol formulation comprises biocontrol agents and bioplastic carrier granules, Mater-Bi® granules. The biocontrol agents of the formulation can comprise non-toxigenic strains of *Aspergillus* spp. which are capable of inhibiting growth of fungi that produce aflatoxin and further capable of suppressing production of aflatoxin by the toxigenic fungi or the biocontrol agents can comprise *Trichoderma virens* strains capable of inhibiting damping off in horticultural plants. The present invention relates to a biocontrol strategy whereby the biocontrol formulation comprising a non-toxigenic *A. flavus* strain and Mater-Bi® is applied to crops as a method for reducing aflatoxin contamination in corn and other crop plants.

2. Description of the Relevant Art

Augmentative biological control is generally perceived as a pest management tactic that utilizes the deliberate introduction of living natural enemies to lower the population level of invasive pests (DeBach and Rosen. 1991. In: *Biological Control by Natural Enemies*, Cambridge University Press, Cambridge). Biological control has been utilized for more than 100 years in efforts to control a wide number of agricultural pests including fungi, insects, and weeds (Siddiqui and Mahmood. 1996. *Biores. Technol.* 58: 229-239; Stiling and Cornelissen. 2005. *Biol. Control* 34: 236-246). Biocontrol strategies have been implemented to control aflatoxin contamination in several important agricultural crops, such as peanut, cotton, and corn (Abbas et al. 2006. Biocontrol Sci. Technol. 16: 437-449; Cotty, P. J. 1994. *Phytopathology* 84: 1270-1277; Dorner et al. 1992. J. Food Protect. 55: 888-892). Aflatoxins are highly carcinogenic secondary metabolites produced by several species of *Aspergillus* section *flavi*, including *A. flavus* Link, *A. parasiticus* Speare, and *A. nominus* Kutzman, Horn and Hesseltime. Of these, *A. flavus* is the most abundant aflatoxin-producing species associated with corn (Abbas et al. 2004a. *Can. J. Bot.* 82: 1768-1775; Abbas et al. 2004b. *Can. J. Microbiol.* 50: 193-199; Abbas et al. 2008. *J. Agric. Food Chem.* 56: 7578-7585; Wicklow et al. 1998. *Mycol. Res.* 102: 263-268). *A. flavus* is readily isolated from diverse environmental samples; however, soil and crop residues are considered the natural habitat of this fungus (Abbas et al. 2008, supra). In addition, soil serves as a reservoir of conidia (spores) which can infect susceptible crops (Scheidegger and Payne. 2003. *Toxin Rev.* 22:423-459).

Management of aflatoxin-producing fungi in corn is a difficult task, requiring an integrated approach including optimization of agronomical practices (i.e. irrigation, fertilization, etc.). These practices promote the general health of corn and can reduce, but not eliminate aflatoxin contamination (Cleveland et al. 2003. *Pest Manag. Sci.* 59: 629-642). Consequently, there is a need for additional, practical and cost-effective strategies to limit aflatoxin contamination of corn (Cleveland et al., supra). One attractive option to supplement, but not supplant these agronomical practices is biological control. Aflatoxin biological control programs can truly be defined as bio-competition since they do not utilize parasites or diseases of the pest, but instead use atoxigenic *Aspergillus* spp. to competitively exclude toxigenic fungi. Further, other fungal biocontrol agents such as *Trichoderma* have the potential to inhibit and displace damping-off fungi and other soil born diseases on a wide range of horticultural crops (Paulitz and Belanger. 2001. *Ann. Rev. Phytopathology* 39:103-133; Elliott et al. 2009. *Biocontrol Sci. Tech.* 10:1007-1021).

Surveys conducted in multiple geographical regions have found that not all strains of *A. flavus* produce aflatoxins (Abbas et al. 2004a, supra; Cotty and Bhatnagar. 1994. *Appl. Environ. Microbiol.* 60: 2248-2251). Current biocontrol strategies rely upon the ability of non-aflatoxigenic strains to competitively exclude indigenous aflatoxin-producing *Aspergilli* (Cleveland et al., supra). Successful reduction of aflatoxin contamination through the introduction of competitive non-aflatoxin producing strains of *A. flavus* has been demonstrated in a number of crops, including corn (Dorner et al. 1992, supra; Dorner, J. W. 2005. In: *Aflatoxin and Food Safety*, Abbas, H. K., Ed., CRC Press, Taylor & Francis Group, Boca Raton, pp. 333-352). Biocontrol fungi are typically applied to soil as alginate pellets, pregelatinized starch-flour granules, or colonized grains (Dorner, J. W. 2008. *Food Addit. Contam.* 25: 203-208; Honeycutt and Benson. 2001. *Plant Dis.* 85: 1241-1248; Lewis et al. 1998. *Plant Dis.* 82: 501-506). Among some of the successful formulations, a pasta-like product (Pesta) and a coated hulled-barley formulation (Afla-Guard®) have proven to be effective for delivering non-aflatoxigenic strains of *A. flavus*, as well as other biocontrol fungi (Connick et al. 1998. *Biol. Control* 13: 79-84; Singh et al. 2007. *Biores. Technol.* 98: 470-473; Dorner, supra). Application of these protocols has also been shown to be highly effective in recent studies conducted by the USDA-ARS at the Stoneville, Miss. research station. In these efforts, Abbas et al. (2006, supra) demonstrated that aflatoxin contamination in corn is dramatically reduced by field application of non-aflatoxin producing *A. flavus* strain NRRL 30797 (K49). In Abbas et al. (2006, supra) conidia of the competitive non-aflatoxigenic strain were applied to soil as inoculated wheat grains.

Various biocontrol methods and formulations for effective control of toxigenic fungi in cotton, peanuts, and corn are known in the art, as discussed above. However, there still remains a need for formulations of biocontrol agents which are effective for ensuring the integrity and effectiveness of the biocontrol agent after long term storage, for facilitating handling, and for field application of the biocontrol agent. Novel granular bioplastic biocontrol compositions comprising non-aflatoxigenic and non-toxigenic *A. flavus* strains and methods of using a novel granular bioplastic biocontrol composition to effectively reduce aflatoxin contamination in corn and other crop plants are provided. The need for suitable formulation systems to deliver other fungi used in biological control of plant diseases is also evident. Thus, an example of the use of bioplastic material to deliver *Trichoderma virens* to control damping-off disease caused by *Rhizoctonia solani* is also disclosed.

SUMMARY OF THE INVENTION

We have invented a biocontrol composition comprising a non-toxigenic fungal strain and the commercial bioplastic granules, Mater-Bi®, and discovered that particular biocontrol formulations comprising biocontrol fungi (non-toxigenic *Aspergillus* strains and *Trichoderma virens*) and bioplastic granules can reduce aflatoxin contamination in corn and Rhizoctonia solani-induced damping off in impatiens, respectively.

In accordance with this discovery, it is an object of the invention to provide a biocontrol composition comprising a non-toxigenic or non-aflatoxigenic fungal strain and bioplastic granules.

It is further object of the invention to provide a biocontrol composition comprising non-toxigenic strains of *Aspergillis* spp. and bioplastic granules.

It is another object of the invention to provide a biocontrol composition comprising the non-toxigenic *A. flavus* strain NRRL 30797 and Mater-Bi® bioplastic granules.

It is still further object of the invention to provide a biocontrol composition comprising a *Trichoderma* strain capable of suppressing damping-off disease and Mater-Bi® bioplastic granules.

It is another object of the invention to provide a method of using the biocontrol composition comprising a non-toxigenic fungal strain and bioplastic granules for biocontrol of toxin-producing fungi in plants.

It is an additional object of the invention to provide a biocontrol method of preventing or reducing aflatoxin contamination of corn which includes applying the biocontrol composition/formulation of the non-toxigenic *A. flavus* strain NRRL 30797 and Mater-Bi® to the soil to control aflatoxin.

Also part of this invention is a kit, comprising the biocontrol composition/formulation comprising Mater-Bi® for application to corn crops to prevent or reduce aflatoxin contamination.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

Figure 1:
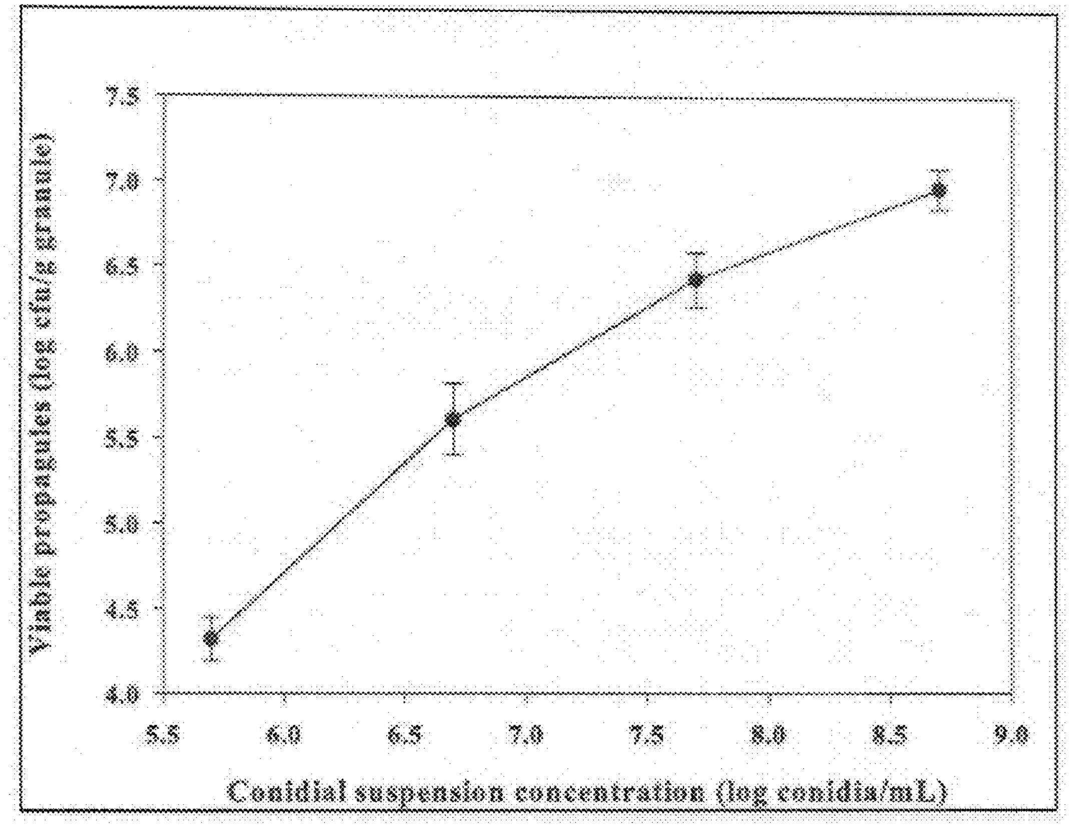
FIG. 1 depicts the effect of conidial suspension concentration on final potency of Mater-Bi® granules. Each point represents mean±STD (n=3).

We have demonstrated that a novel biocontrol composition comprising Mater-Bi® (MB) granules and a biocontrol strain, e.g., *A. flavus* NRRL 30797, is effective for introducing a stable population of the biocontrol strain into soil. The method of using a biocontrol composition comprising a bioplastic material for carrying the biocontrol fungi is novel. The bioplastic product MB has a comparable efficiency for delivering Aspergilli propagules in the soil to the widely used formulations employing the wheat-flour based Pesta. The easy and rapid process proposed here for entrapping Aspergilli into MB granules, as well as the favorable physical characteristics of the granules, makes MB a practical option for delivering the non-aflatoxigenic *A. flavus* NRRL 30797 strain in the field. MB granules are also adaptable for use in carrying other biocontrol fungi (i.e. *Trichoderma* spp., etc.).

Mater-Bi® (MB) is a bioplastic product composed of starch, polycaprolactone (ϵ-caprolactone), and a minor amount of a natural plasticizer (Bastioli, C. 2001. *Starch/Starke* 53:351-355). MB is a reliable and readily adaptable product that is currently used for making shopping bags, biofillers, agricultural films, and a number of other commercial products (Bastioli 2001, supra). MB is completely biodegradable having a rate of breakdown similar to that of cellulose (Bastioli, C. 1998. *Polym. Degrad. Stabil.* 59: 263-272). In addition to the highly favorable low environmental impact profile, its physical properties facilitate product handling and field application. These properties make granular MB an excellent candidate for biocontrol applications of *Aspergillus* propagules. Therefore, we report a series of studies demonstrating the reliability of MB granules as substrate for delivering conidia of the non-aflatoxigenic strain of *A. flavus* NRRL 30797 in soil. The composition of the invention encompasses bioplastic granules having the same identifying characteristics as Mater-Bi® bioplastic granules.

The effectiveness of the novel MB-biocontrol strain composition has been demonstrated under controlled conditions (i.e. soil moisture, air temperature, etc.) and confirmed under field conditions. The Mater-Bi technology is shown to be adaptable to other fungal biocontrol agents, namely, *Trichoderma.*

The addition of highly competitive non-toxigenic strains of *A. flavus* to soil results in lower concentrations of toxins in agricultural crops. The non-toxigenic strains of *Aspergillus* become biocompetitive with the soil's microflora and prevent the buildup of toxin-producing strains. Through biocompetition the toxigenic strains of fungi found naturally in soil are replaced by non-toxigenic or non-aflatoxigenic strains added to the soil. Therefore, crops are invaded predominately by the biocompetitive strains which are unable to produce toxins.

The method of the invention is applicable to any agricultural commodity which is grown for human consumption and/or which is damaged by fungal toxins such as peanuts, corn, cotton, tree nuts, vegetable plants, and ornamental plants susceptible to damping off.

For purposes of this invention a fungal preparation or fungal agricultural biocontrol composition refers to a microbial preparation wherein the microbes comprise, consist essentially of, or consist of non-toxigenic or non-aflatoxigenic strains of *Aspergillus* and of *Trichoderma* strains capable of suppressing damping-off disease. The fungal preparations may contain one or more of non-toxigenic strains or non-aflatoxigenic strains of *Aspergillus*. Non-toxigenic strains of *Aspergillus* include any strain which does not produce the toxins aflatoxin and cyclopiazonic acid (CPA). The agricultural biocontrol composition for purposes of this invention, includes a non-toxigenic strain or strains of fungi on agriculturally acceptable carriers which may be any carrier which the fungi can be attached to and are not harmful to the fungi or crops are treated with the composition. An example of a non-toxigenic strain includes *A. flavus* K49. The fungi especially useful in the present invention, are strains possessing the identifying characteristics of non-toxigenic *A. flavus* K49, designated NRRL 30797. These characteristics are the inability to produce the toxins aflatoxin and CPA and the ability to be biocompetitive when applied to soils growing agricultural commodities.

Non-aflatoxigenic strains of *Aspergillus* include any strain which does not produce the toxin aflatoxin, but which continues to produce cyclopiazonic acid (CPA). The agricultural biocontrol composition, for purposes of this invention, can include a non-aflatoxigenic strain or strains of fungi on agriculturally acceptable carriers which may be any carrier the fungi can be attached to and are not harmful to the fungi or crops that are treated with the composition. An example of a non-aflatoxigenic strain includes *A. flavus* CT3. The fungi that are especially useful in the invention are strains possessing the identifying characteristics of the non-aflatoxigenic *A. flavus* strain CT3, designated NRRL 30798. These characteristics are the inability to produce aflatoxin and the ability to be biocompetitive when applied to soils growing agricultural commodities.

As discussed earlier, non-toxigenic and aflatoxigenic strains of *Aspergillus* have been cultured as single strain on granular food sources, such as wheat, rice, rye, etc. These food sources contain approximately $10^6$ colony forming units (CFU) of fungi per gram of food source. Some successful formulations in use are Pesta, a pasta-like product, and a coated hulled-barley formulation (Afla-Guard®).

The non-toxigenic and non-aflatoxigenic strains of *Aspergillus* are applied to soil in amounts effective to reduce toxin levels in agricultural commodities. As used herein "reduce toxin levels" refers to a reduction in amounts of toxin compared to that which would be expected in agricultural commodities which were not treated according to the methods of the present invention. Any accurate method of measuring and comparing toxin levels may be used for such comparisons as would be apparent to those skilled in the art.

As used herein, "in amounts effective, an amount effective or an effective amount" refer to the amount of the fungal preparation administered wherein the effect of the administration acts to reduce toxin contamination of agricultural commodities. The granular or extruded products are applied to the soil at a rate of approximately 5 to 30 kilograms (kg) per hectare (ha). The soil surface around the plant provides a humid, protected environment which promotes growth and sporulation of the non-toxigenic and non-aflatoxigenic fungi. The strains can be applied as single strain compositions or the dried products can be mixed in about equal proportions to provide a composition made up of different strains of *Aspergillus*.

EXAMPLES

Having now generally described this invention, the same will be better understood by reference to certain specific examples, which are included herein only to further illustrate the invention and are not intended to limit the scope of the invention as defined by the claims.

Example 1

*Aspergillus flavus* Strains and Soil

Two strains of *A. flavus* were selected for this study; the non-aflatoxigenic strain *A. flavus* NRRL 30797 (K49) and the aflatoxin-producing *A. flavus* NRRL 30796 (F3W4). Properties of the two strains have been previously described (Abbas et al. 2006, supra; Accinelli et al. 2008. *Canad. J. Microbiol.* 54: 371-379). Fresh conidia were generated by plating $10^8$ spores per ml on acidified potato dextrose agar (PDA) and incubating at 37° C. for 5-7 days. A total of 5 ml of sterile 0.2% Tween 20 was added per plate, and conidia were collected by gentle scraping. Conidia concentration was determined using a hemocytometer and adjusted as necessary.

Soil used in this study was collected on December 2007 from a 1-ha uncropped area located at the experimental farm of the University of Bologna, Italy. The soil was classified as a Cataldi silty loam (Udic Ustochrepts, fine silty, mixed, mesic) with 380 g/kg sand, 245 g/kg clay, 375 g/kg silt, 8.5 g/kg organic C, and pH (1:2.5 soil/water mixture) of 8.0. A total of ten soil samples (5-20 cm depth) were arbitrarily collected using a sterilized spatula. These ten samples were bulked together, homogenized by passing through a 4-mm sieve, and stored at 4° C. until processed. A sufficient mass of soil was autoclaved at 120° C. for 60 min on three successive days.

Example 2

Preparation of the Mater-Bi®-*A. flavus* Biocontrol Composition; Preparation of Pesta Granules Granules of Mater-Bi® ZF03U/A (MB) with average size of 5 mm long and 3 mm diameter were supplied by Novamont S.p.A. (Novara, Italy). Conidia from the *A. flavus* NRRL 30797 were entrapped within the MB granules by equilibrating the granules in conidial suspensions ranging from log 5.7 to log 8.7 conidia/mL for 4-hours with shaking (300 rpm). After this incubation, the conidial suspensions were then forced through these impregnated granules using a piston-like device at a pressure of 62 kPa (Riff98, Italy). Finally, granules were dried at 40° C. for 2 hours and surface cleaned by flushing compressed air generated from a commercial air-compressor. The total number of entrapped *A. flavus* conidia in the granules was evaluated by plate count. Evaluations of colony forming units on granular surface, shelf life of granules, and MB ability to support growth and sporulation were determined as described below.

Pesta granules were prepared as described in Connick et al. (1998, supra) with minor modifications. Briefly, 32 g of semolina (Barilla, Italy), 8 g of kaolin (Merck, Germany) and 21 ml of a conidia suspension (strain K49) were manually kneaded to make dough. The dough was extruded through a Rosle potato masher and cut to obtain cylindrical granules of the same size of MB granules. After drying at 40° C. for 2 hours, Pesta granules were transferred into screw-top tubes and stored in the dark at 5° C. and 20° C. Soil samples containing a single Pesta granule were prepared and incubated as described for MB granules.

Example 3

Enumeration of *A. flavus* Colony Forming Units on the Surface of Mater-Bi® Granules Another essential prerequisite for any biopesticide is that it should be safe for operators. Even though *A. flavus* NRRL 30797 is a proven non-aflatoxigenic strain (Abbas et al. 2006, supra), our efforts were directed to making a solid formulation with fungal propagules mostly entrapped within the granules in order to reduce risks of mold inhalation during handling and field application.

Estimates of the percentage of *A. flavus* conidia located on the granule surface were determined by exposing the granules to UV rays for 60 min using a model G20T10 UV germicidal lamp (Sankyo Denki, Japan). The difference in the total colony forming units (cfu) of unexposed and UV exposed granules gave an estimation of the propagules present on the granule surface after air-pressure cleaning.

Exposing granules to germicidal UV light led to a 25% decrease of recoverable propagules, thus confirming that most of the conidia are located within the granules (data not shown).

Example 4

Enumeration of *Aspergillus flavus* Propagules in MB Granules

The *Aspergillus* conidia-carrying capacity of MB granules was evaluated relative to the widely used granular formulation Pesta, which consist of a wheat gluten-kaolin matrix encapsulating fungal propagules. Enumeration of *A. flavus* conidia present in MB and Pesta granules was achieved by placing single granules in centrifuge tubes containing 10 ml of phosphate buffer saline (PBS) and 5 g of glass beads, vortexing for 5 min, agitating for 2 hr at 200 rpm, and serially diluted the resulting suspension in PBS prior to plating. Suspensions were diluted in triplicate and 100-μL aliquots were spread onto modified rose bengal agar (MDRBA) as per Abbas et al. (2004b, 2006, supra). Plates were incubated at 37° C. for 4-5 days and the resulting *A. flavus* colonies were recorded. For enumeration of total culturable fungi in MB and Pesta granules, MDRBA was replaced with acidified potato dextrose agar and incubated at 25° C.

Equilibrating MB granules with conidia suspensions ranging from log 5.7 to 8.7 conidia/mL resulted in a range of propagules of log 4.3 to 7.0 cfu per granule, respectively (FIG. 1). Considering that effective biocontrol formulation depends on the potency (number and ability to produce propagules), we focused on the MB granules generating the highest propagule rate (i.e. highest potency).

Example 5

Comparison of Shelf Life of *A. flavus*-MB Composition and Pesta Granules

For shelf life evaluation, granules were transferred into Zip-loc plastic bags (1-1 volume) and stored in the dark at 5° C. and 25° C. After 3 and 6 month-storage, colony viability was evaluated by plate count.

Figure 2:
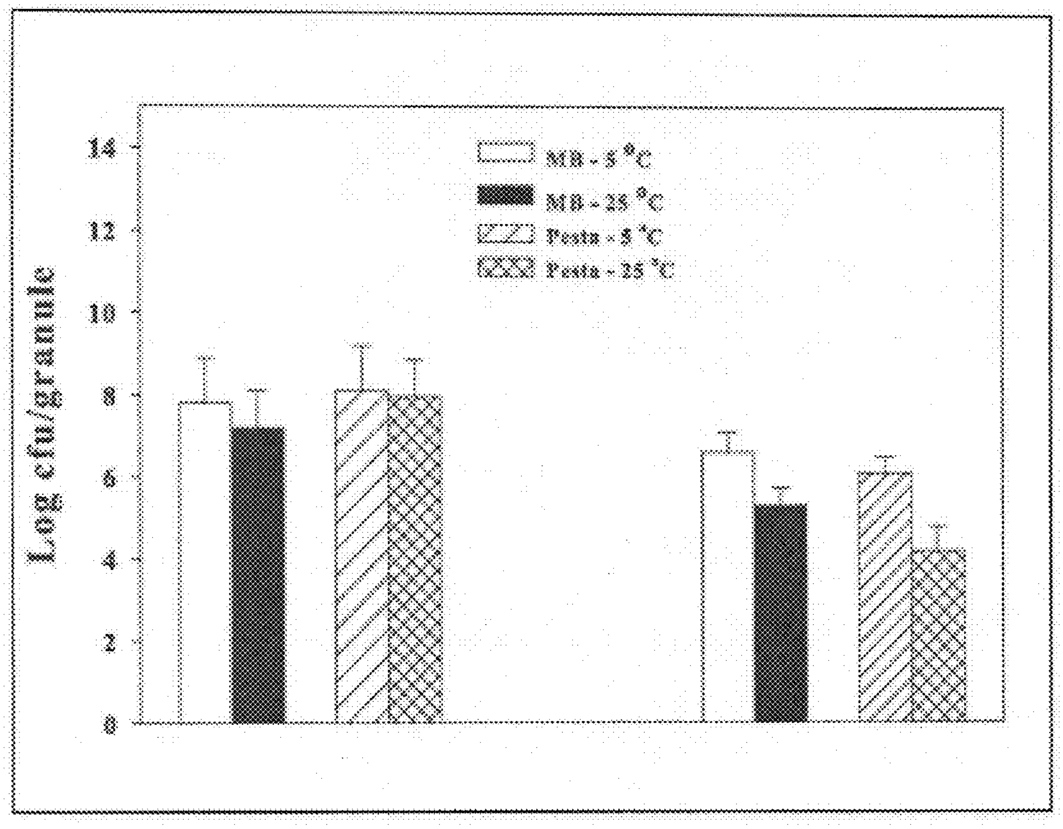
FIG. 2 shows the effect of temperature and storing time on shelf life of Mater-Bi® and Pesta granules inoculated with conidia of the *A. flavus* NRRL 30797. Initial potency of MB and Pesta granules was of log 8.7 cfu per granule. Each bar represents mean±STD (n=3).
Figure 3:
FIG. 3 depicts Pesta (left) and Mater-Bi® (right) granules after six month of storing in plastic bags.

As seen in FIG. 2, after storing inoculated MB granules for six months at 5° C. and 25° C., the number of viable *A. flavus* NRRL 30797 propagules declined approximately 75% and 95%, respectively. No significant decline was observed in MB granule stored for a shorter period (three months) at either temperature. As expected, MB granules maintained their physical integrity over the whole six month storing period (FIG. 3). This is consistent with the physical properties of MB, which are similar to those of traditional petrol-based plastic matrices (Bastioli 1998, supra).

Pesta granules showed a comparable shelf-life to MB granules (FIG. 2), showing declines of approximately 90% and 60% for 5° C. and 25° C. at 6 months, respectively. Beside intrinsic factors influencing conidia viability, Pesta granules are made of semolina-based materials which results in an easily breakable product (FIG. 3). This implicates that a decrease of the initial product potency caused by handling, storing and field application could not be excluded. In contrast, MB granules are highly resilient to these same types of damage, and thus need no particular precautions to prevent loss of potency.

Example 6

Biodegradation Pattern of MB Granules and Pesta Granules in Soil

Figure 4:
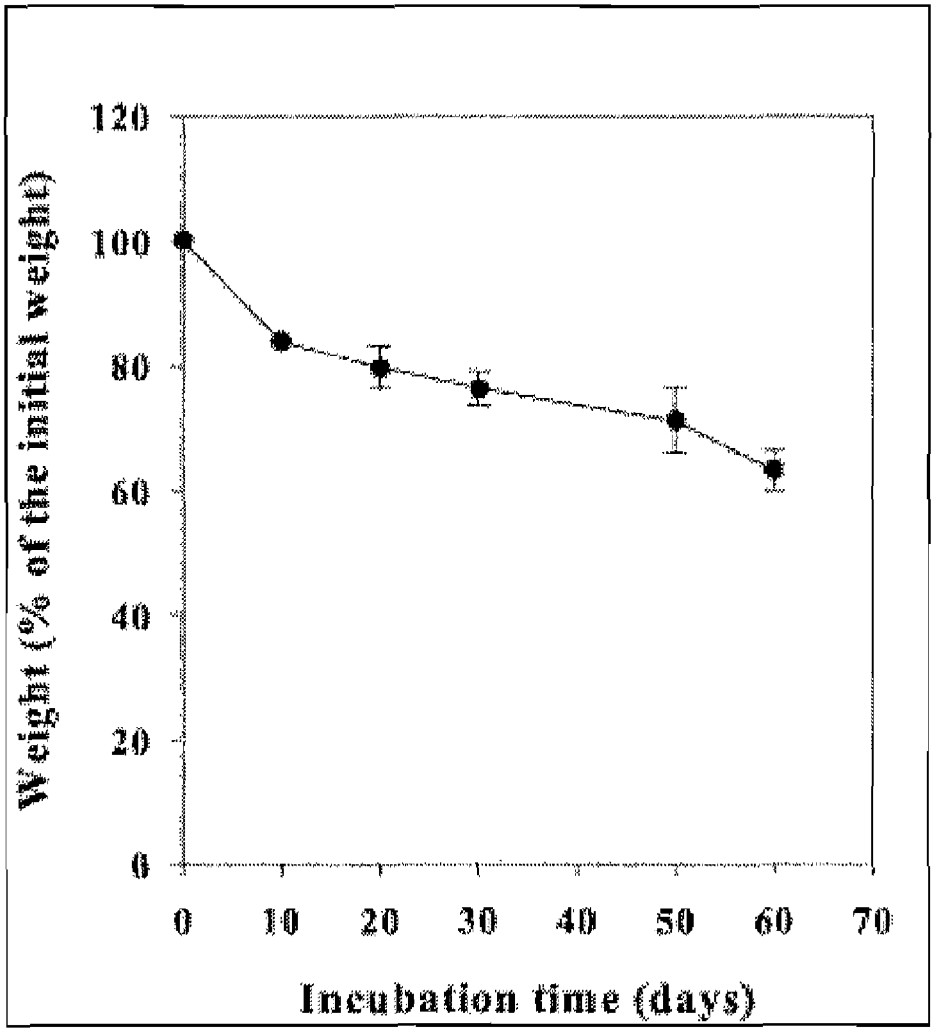
FIG. 4 shows the biodegradation of Mater-Bi® granules in soil expressed as percentage of the initial weight. Each point represents mean±STD (n=3).

Biodegradation pattern of MB granules in soil is depicted in FIG. 4. Approximately 40% of the granule weight was lost during the 60-day incubation period. As expected, Pesta granules showed a more rapid degradation. After 10 days of incubation, Pesta granules were almost completely disintegrated; thus it was not possible to accurately measure their weight. The biodegradation rate of MB granules reported here is comparable with those reported by other authors (Kim et al. 2000.; Mezzanotte et al. 2005. *Polym. Degrad. Stabil.* 87: 143-151; Rutkowska et al. 2004. *Pol. J. Environ. Stud.* 13: 85-89).

Example 7

DNA Analysis

A series of DNA-based methods were used for tracking the introduced *A. flavus* strain NRRL 30797 in incubated soil samples. These include PCR with known aflatoxin biosynthetic gene primers, qPCR of the biosynthetic gene omtB (aflO), and PCR of internal transcribed spacers.

PCR-based detection of *A. flavus* DNA in soil was achieved following the procedure described in Accinelli et al. (2008, supra). Briefly, total soil DNA was isolated using the commercial kit PowerSoil (MoBio Laboratories Inc., Solana Beach, Calif.) and purified with the Wizard DNA Clean-Up System (Promega, Wis.), following the instructions of the manufacturers. Eluted DNA was used for PCR analysis for detecting five genes of the aflatoxin biosynthesis pathway (Table 2). The PCR reaction mixture contained 25 μL of RedTaq ReadyMix (Sigma-Aldrich), 0.5 μM of each primer (Operon Biotechnologies, Germany), 5-10 ng template DNA and water to a final volume of 50 μL. The cycling was performed with the T3 DNA thermalcycler (Biometra, Germany) as follows: 94° C. (4 min) followed by 30 thermal cycles of 94° C. (30 s), 56° C. (30 s), 68° C. (60 s), and a final elongation step at 72° C. for 15 min. The amplified products were separated on a 1% agarose gel and visualized by staining with SYBR Green I (Sigma-Aldrich).

added to tubes. Tubes were gently shaken and centrifuge at 10,000×g for 5 min before the addition of ⅔ vols of isopropanol/ammonium acetate to precipitate the DNA. The pellet was rinsed with 70% ethanol, air dried and resuspended in 100 μl, of TE buffer.

DNA amplification was performed using a primer set that targets the aflatoxin cluster gene OmtB (aflO) (Table 1). Efficiency of qPCR was tested by including amplification of the laeA gene, a global regulator gene of the secondary metabolism in Aspergilli, as indicated in Kim et al. (2008, supra). DNA isolated from soil samples treated with 10-fold dilutions of *A. flavus* NRRL 30797 conidial suspension, as described above, was utilized as template for 25 μL qPCR reactions. Each 25 μL qPCR reaction contained 2 μL of DNA, 12.5 μl of

TABLE 1

Primer sequences of genes tested by PCR and qPCR.

| Gene | Primer sequence | PCR product size (bp) | Reference |
|---|---|---|---|
| aflD-F | 5'-ACGGATCACTTAGCCAGCAC-3' | 990 | Scherm et al.[a] |
| aflD-R | 5'-CTACCAGGGGAGTTGAGATCC-3' | | Scherm et al.[a] |
| aflO-F | 5'-GCCTTGACATGGAAACCATC-3' | 1330 | Scherm et al.[a] |
| aflO-R | 5'-CCAAGATGGCCTGCTCTTTA-3' | | Scherm et al.[a] |
| aflP-F | 5'-GCCTTGCAAACACACTTTCA-3' | 1490 | Scherm et al.[a] |
| aflP-R | 5'-AGTTGTTGAACGCCCCAGT-3' | | Scherm et al.[a] |
| aflQ-F | 5'-CGACTGTTGGCCTTTTCATT-3' | 1088 | Scherm et al.[a] |
| aflQ-R | 5'-ATAGCGAGGTTCCAGCGTAA-3' | | Scherm et al.[a] |
| aflR-F | 5'-CGAGTTGTGCCAGTTCAAAA-3' | 999 | Scherm et al.[a] |
| aflR-R | 5'-AATCCTCGCCCACCATACTA-3' | | Scherm et al.[a] |
| ITS1-F | 5'-TCCGTAGGTGAACCTGCGG-3' | ~1100 | O'Donnel[b] |
| ITS4-R | 5'-GGTCCGTGTTTCAAGACGG-3' | | O'Donnel[b] |
| omtB-F | 5'-AAGCAGATCATCCCAGTGAT-3' | ~130 | Kim et al.[c] |
| omtB-R | 5'-CGAGTTGTGCCAGTTCAAAA-3' | | Kim et al.[c] |
| laeA-F | 5'-GCTGGTACAATTTGGCTGTC-3' | ~130 | Kim et al.[c] |
| laeA-R | 5'-CGCCTCCGACTTGACTTCTG-3' | | Kim et al.[c] |

[a]Scherm et al. 2005. Int. J. Food Microbiol. 98: 201-210.
[b]O'Donnel. 1993. In: The Fungal Holomprph: Mitotic, Meiotic and Pleomorphic Speciation in Fungal Systematic, Reynolds & Taylor (Eds.), CAB International, Wallingford, pp. 225-233.
[c]Kim et al. 2008. Int. J. Food Microbiol. 29: 49-60

Total *A. flavus* DNA in incubated soil samples was estimated by qPCR. In addition, a selected number of samples were also analyzed to quantify total *A. flavus* DNA remaining in MB granules during the 60-day incubation period. Soil DNA was isolated using the same procedure adopted for PCR analysis. DNA isolation from MB granules was performed following the CTAB procedure, with minor modifications (Doyle and Doyle. 1990. *Focus* 12: 13-15). Briefly, two MB granules were removed from soil samples, dried at 40° C. for 2 hours, vortexed for 5 min, and air-flushed by high-pressure air. Surface-cleaned granules were transferred to a 2-mL microcentrifuge tube containing 500 μL of CTAB buffer and glass beads (425-600 μm; Sigma-Aldrich). After vortexing for 2 min, tubes were incubated at 65° C. for 15 min, and an equivalent volume of chloroform:isoamyl alcohol (24:1) was 2× TaqMan Universal PCR Master Mix (Applied Biosystems, CA), and 0.2 μM of each primer. Thermocycling conditions were as follows: 2 min at 50° C., 10 min at 95° C., and 40 cycles of 15 s at 95° C. and 1 min at 60° C. The resulting samples were analyzed using an ABI Prism 7700 Sequence Detection System (Applied Biosystem). After quantification, amplified fragments samples were subjected to melting-curve analysis. A standard curve was generated by plotting cycle threshold values (Ct) against logarithmic-transformed amounts of target DNA obtained from 10-fold dilutions of DNA isolated from *A. flavus* NRRL 30797. Correlation between amount of target DNA recovered from soil and the size of *A. flavus* propagules (estimated by plate count) was calculated.

At the end of the 60-day incubation period, diversity of the soil fungal community was estimated by rDNA internal spacer analysis (RISA). Soil DNA was isolated as described previously and amplified using the universal fungal primers ITS1/ITS4 targeting the internal transcribed (ITS) region (Table 1). Ten microliters of PCR products were digested with 10 units of Hae III in a total volume of 25 μL at 37° C. for 2 hours, and the digested products were separated by vertical nondenaturing 8% polyacrylamide gel electrophoresis and visualized by SYBR Green I staining.

Example 8

Ability of *A. flavus*-MB Composition/Formulation to Support Growth and Sporulation The potential of MB matrix to support *A. flavus* growth and sporulation was evaluated by inoculating 200 untreated pre-wetted MB spherical granules (2 mm diameter) with 1.5 ml of a *A. flavus* NRRL 30797 conidial suspension (log 2.7 conidia ml-1) and incubating on Petri plates (45 mm) at room temperature. At selected intervals, fungal colonization of MB granules was estimated by visual observation and quantitative PCR (qPCR).

Figure 5:
FIG. 5 shows the growth of *A. flavus* NRRL 30797 (K49) on inoculated Mater-Bi® granules (1-2 mm diameter) (left) and in untreated (control) granules (right).

Research has shown that Aspergilli can grow on a wide range of carbon-rich substrates, including bio-plastic materials (Bergenholtz and Nielsen. 2002. *J. Food Sci.* 67: 2745-2749; Kim et al. 2000, supra). Quantitative PCR analysis and visual observation demonstrated that MB granules adequately supported fungal growth (Table 2; FIG. 5). In contrast to Pesta, no detectable levels of unwanted molds were found in NRRL 30797-inoculated MB granules (data not shown). Pesta is a wheat flour-based produce that is commonly rich in other molds. This is an aspect of great importance due to the fact that these contaminating fungi have the potential to be mycotoxin producing fungi (*Aspergillus* spp., *Fusarium* spp., etc.).

TABLE 2

Total amount of *A. flavus* NRRL 30797 DNA isolated from incubated Mater-Bi ® granules over time.

| DAYS | | |
|---|---|---|
| 0 | 5 | 15 |
| 12.43 ± 3.95* | 62.11 ± 6.23 | 127.99 ± 8.97 |

*Amount of target DNA × $10^3$ fg/

Figure 6:
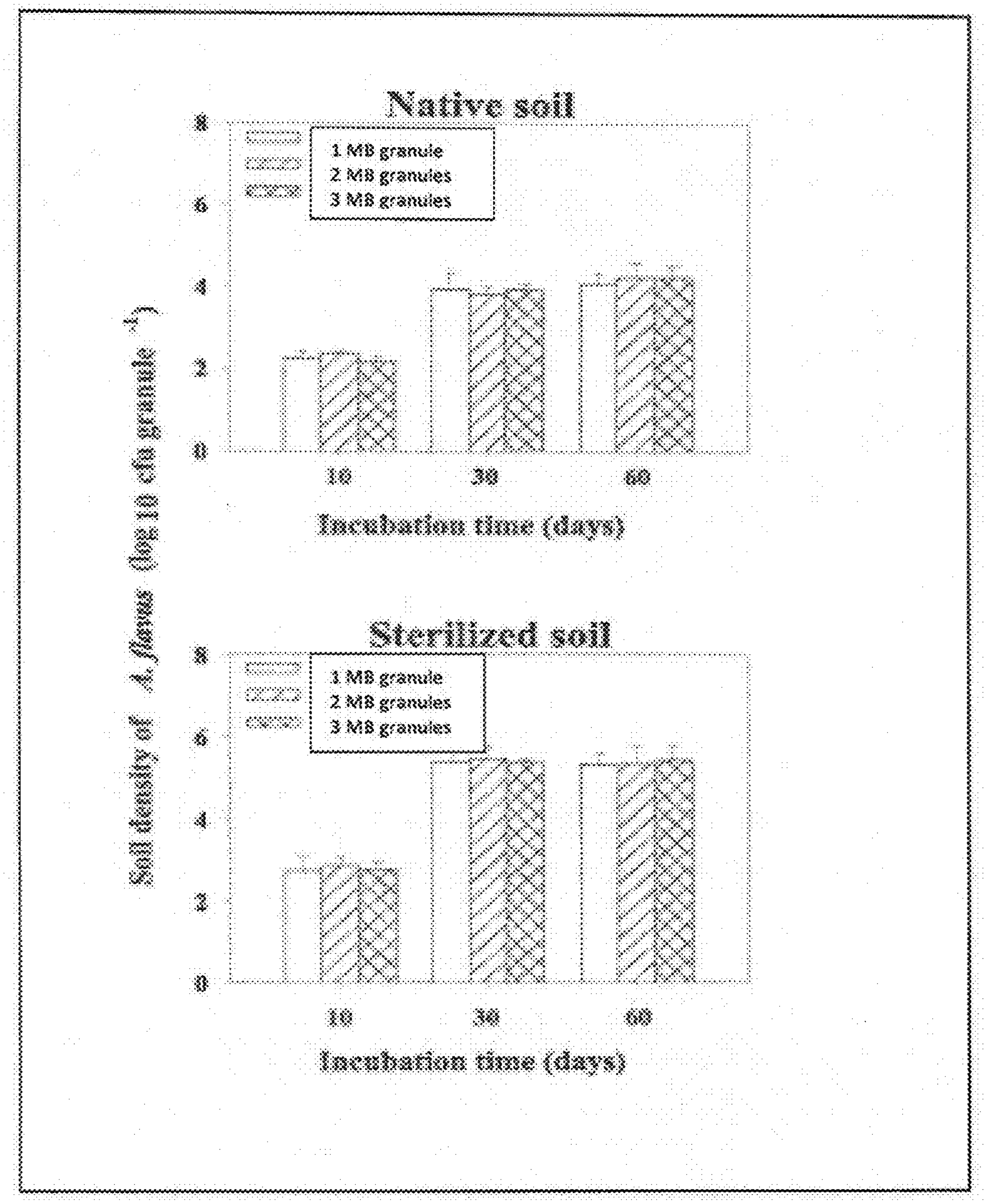
FIG. 6 depicts the colonization of native and sterilized soil by *A. flavus* NRRL 30797 introduced as Mater-Bi® (MB) granules. Each point represents mean±STD (n=3), background propagule density of *A. flavus* in non-inoculated soil remained <log 1.7 cfu/g soil.
Figure 7:
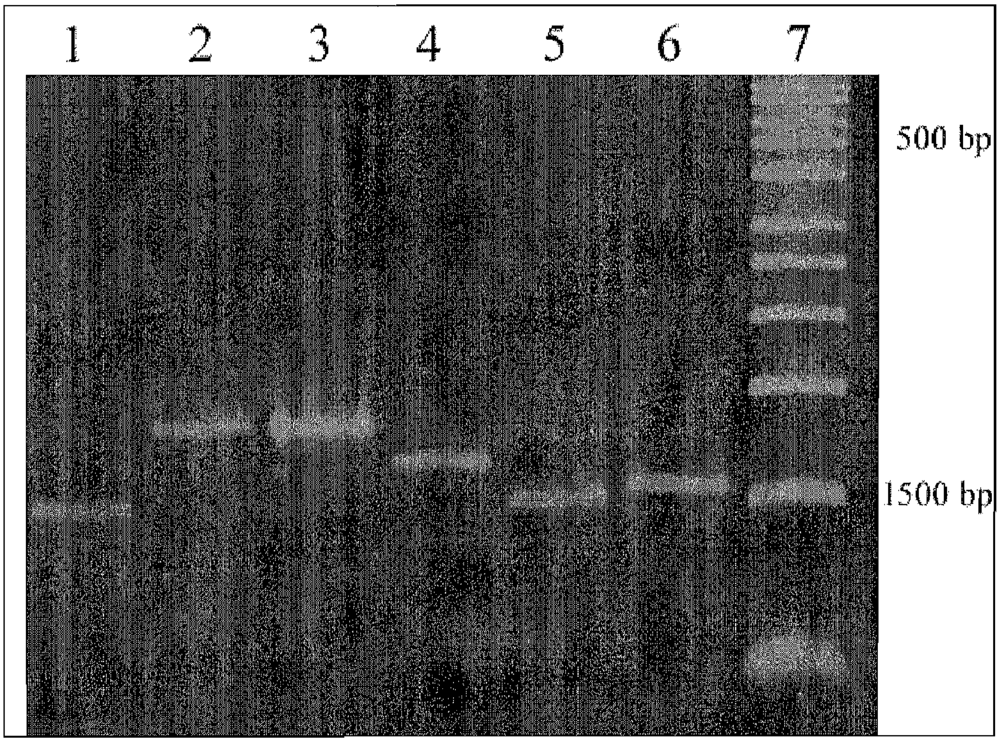
FIG. 7 shows the amplification profile of aflatoxin biosynthesis genes. Lane: 1 aflD, lane 2: aflO, lane 3: aflP, lane 4: aflQ, lane 5: aflR, lane 6: ITS (positive control), lane 7: 1 kb ladder.

Dynamics of soil colonization by the introduced *A. flavus* in MB granules is shown in FIG. 6. Plate counting and PCR analysis showed detectable levels of *A. flavus* by the first sampling time (10 days of samples incubation) (FIG. 6 and FIG. 7). The total size of *A. flavus* population increased during the first month of sample incubation. By day 30, NRRL 30797 was well established and remained present throughout the remaining incubation period. More rapid soil colonization was observed in samples containing single Pesta granules than single MB granules. The findings are likely due to the high content of farinaceous substance found within Pesta, which are known to promote rapid fungal growth (Connick et al. 1998, supra). As Pesta granules are completely disintegrated within 10 days of introduction to soil, no secondary reservoir inoculum is available compared to MB granules, which can maintain a prolonged availability of propagules. However, at the end of the incubation period (60 days), *A. flavus* populations were not significantly different between Pesta and MB samples. It is apparent that the bioplastic matrix supports fungal growth (FIG. 5), but the resulting slow build up of *A. flavus* propagules may be due to the slower biodegradation rate in soil.

Example 9

Competition of *A. flavus*-MB Composition with Soil Populations of *A. flavus*

To determine the number of *A. flavus* propagules in soil and the relative abundance of atoxigenic isolates, the method described in Abbas et al. (2004b, supra) was used with minor modifications. Briefly, soil samples (10 g) were suspended in a 90-ml water agar solution (0.2%), vortex for 3 min, and shaken for 1 hour at 250 rpm. The suspension was used for ten-fold serial dilutions prepared in PBS, and 100-μL aliquots were plated onto MDRBA and incubated at 37° C. for 4-5 days. A sufficient number of colonies (10-30) of *A. flavus* were randomly selected and transferred to β-cyclodextrin (0.3%) potato dextrose agar; the new plates were incubated at 28° C. for 5 days in the dark. Aflatoxin-producing isolates were identified as colonies that displayed blue fluorescence during exposure to UV light (365 nm). Aflatoxin production was confirmed by observing color change of isolates exposed to aqueous ammonium hydroxide (27% v/v) for 30 min.

To estimate soil colonization rate, soil samples were prepared by weighing 20 g of soil in 50-mL sterilized screw-top tubes and moisture adjusted (sterilized distilled water) to the gravimetric content at −33 kPa. Freshly prepared MB granules (1, 2, or 3) were transferred to tubes and samples were homogenized by gently mixing. The samples were incubated in the dark at 25° C. for up to 60 days with soil moisture maintained by weighing samples every 7 days and adding water as needed. At selected intervals, triplicate samples were removed and *A. flavus* colonization estimated by plate count and qPCR. Samples containing three MB granules were also used for estimating biodegradation rate of granules in soil by measuring their weight loss during the 60-day incubation period. To remove soil attached to the granule surface, granules from each sample were transferred to microcentrifuge tubes containing distilled water and glass beads (425-600 μm; Sigma-Aldrich, Germany). Samples were vortexed for 5 min and the slurry removed from tubes to recover the MB granule. The washing process was repeated if required. The washed granules were dried at 40° C. for 2 hours and weighed.

To assess the ability of *A. flavus* strain NRRL 30797 introduced as MB granules to compete with soil populations of *A. flavus*, experiments were conducted with native and sterile soil. Single granules were replicated in soil with artificially established population of the aflatoxigenic *A. flavus* strain NRRL 30796. To establish the *A. flavus* populations, the soil samples were inoculated with NRRL 30796 conidia and incubated for 2 months to establish a population of ~log 2.9 cfu/g soil. As in the soil colonization study, one to three MB granules inoculated with the strain NRRL 30797 were introduced in each 20-g soil sample. Samples were incubated as previously described and relative abundance of toxigenic isolates was estimated as described below.

Figure 8:
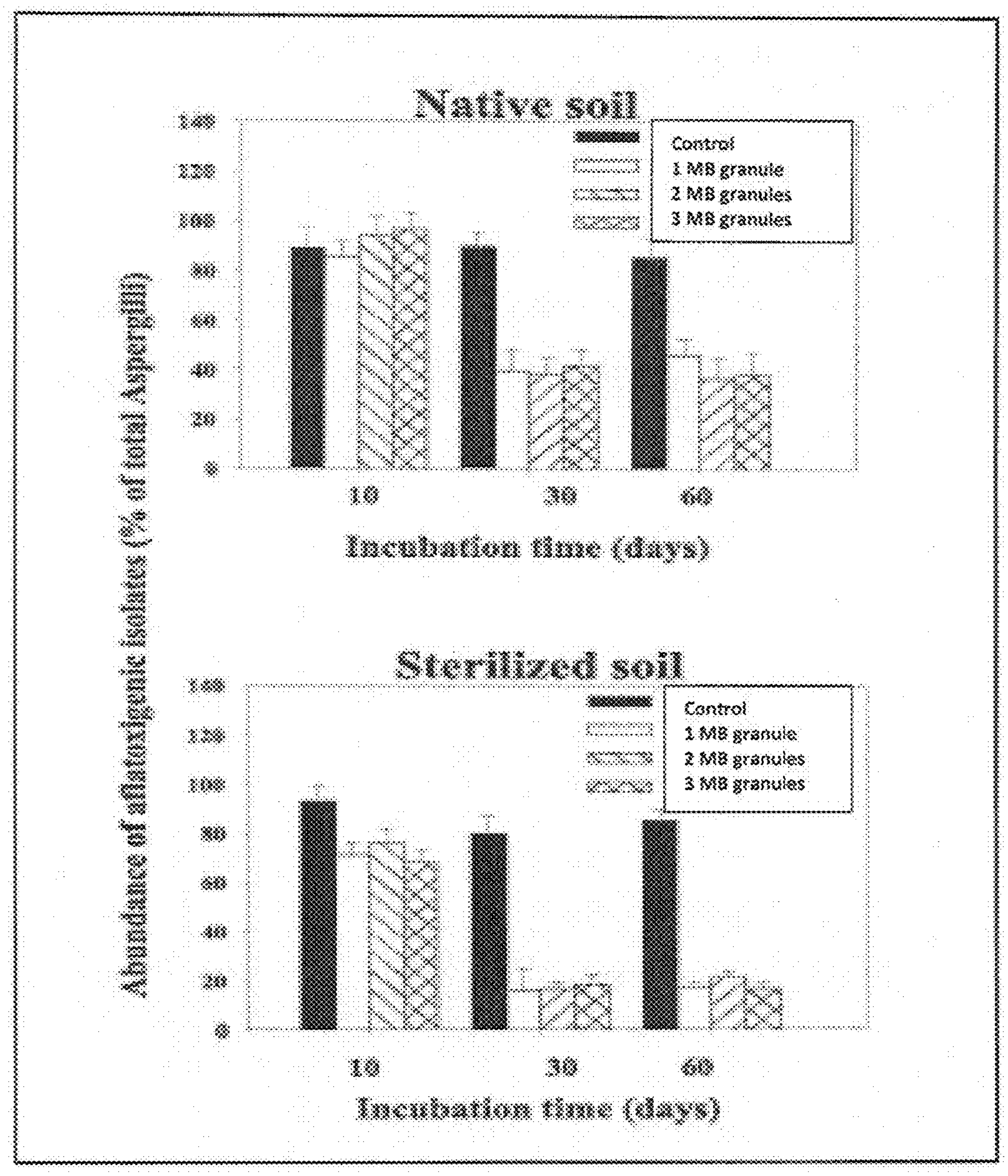
FIG. 8 shows the ability of non-aflatoxigenic strain *A. flavus* NRRL 30797 colonized Mater-Bi® (MB) granules to competitively displace aflatoxin-producing strain *A. flavus* NRRL 30796 previously established in native or sterilized soil.
Figure 9:
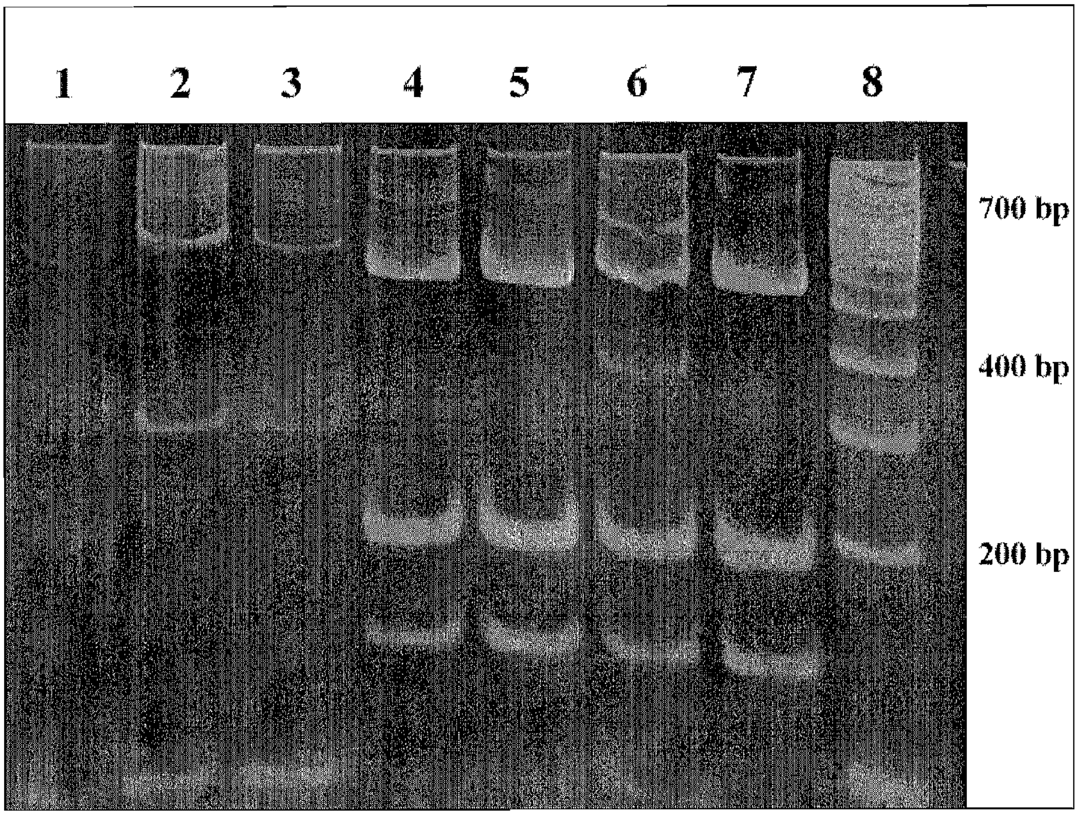
FIG. 9 depicts ribosomal DNA internal spacer analysis of native and sterilized soil samples receiving an increasing number of Mater-Bi® (MB) granules. Lanes 1, 2, and 3: samples of native soil containing 1, 2, and 3 MB granules, respectively. Lanes 4, 5, and 6: samples of sterilized soil receiving 1, 2, and 3 MB granules respectively. Lane 7: *A. flavus* NRRL 30797, lane 8: 100 bp DNA ladder.

Relative abundance of non aflatoxin-producing isolates in soil samples inoculated with the toxigenic strain NRRL 30796 (F3W4) is reported in FIG. 8. Addition of MB granules containing the non-aflatoxigen *A. flavus* strain NRRL 30797 resulted in decreased frequency of aflatoxigenic isolates over the 60-day incubation period, indicating a displacement of aflatoxigenic strain NRRL 30796. The greater ability of the isolate NRRL 30797 to colonize and propagate in the soil in respect to the aflatoxin-producing strain NRRL 30796 has been previously demonstrated (Abbas et al. 2006, supra). However, increasing the number of MB granules did not result in a decrease in aflatoxin-producing isolates. These findings are consistent with the results of the soil colonization experiment discussed above; increasing the number of propagules of the biocontrol strain was not followed by a significant increase of Aspergilli in soil. Similar results have been seen in work involving *Verticillium chlamydosporium* by Mauchline et al. (2002. *Appl. Environ. Microbiol.* 68: 1846-1853) who concluded that competition for nutrients between the introduced and natural occurring microorganisms is the major factor limiting growth of the biocontrol fungus. In addition to reduction of the toxigenic strain, RISA digested ITS-PCR products demonstrated that by 30-days of incubation the diversity of the total fungal community had decreased, resulting in a predominance of *A. flavus* NRRL 30797 (FIG. 9). Soil colonization by the biocontrol strain and reduction of the aflatoxigenic strain was significantly greater in sterilized soil than in native soil (FIG. 8). Similar rapid and intense colonization of sterilized soil by other introduced biocontrol fungi has been reported in the literature (Elad et al. 1981. *Plant Soil* 60: 245-254; Papavis. 1985. *Annu. Rev. Phytopathol.* 23: 225-233) and has been attributed to the reduced inter-specific competition of fungal species in sterilized soil (Leandro et al. 2007. *Appl. Soil Ecol.* 35: 237-246).

Figure 10:
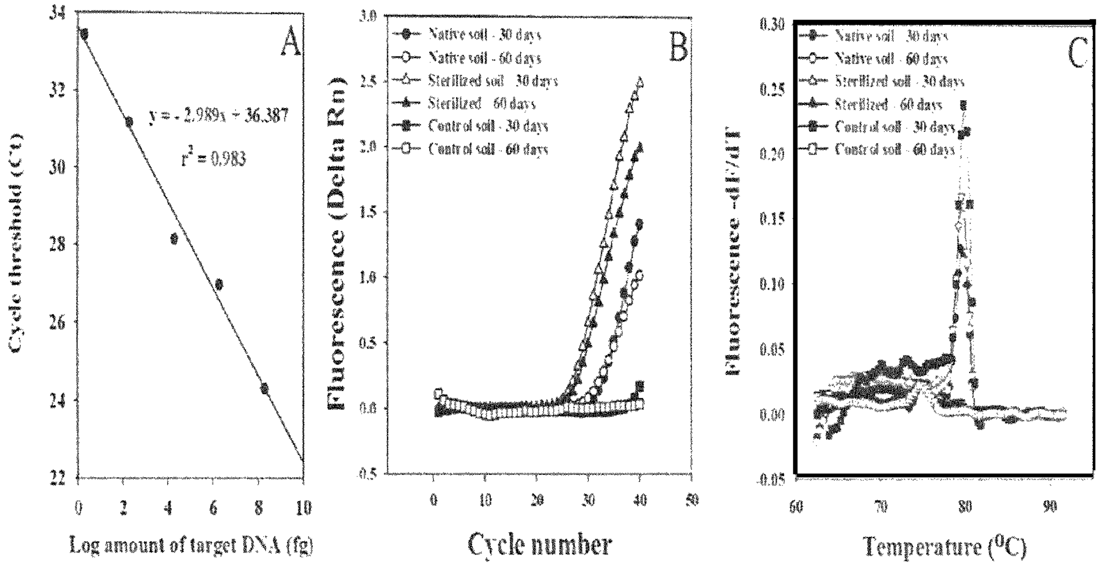
FIG. 10 depicts a standard curve quantifying DNA of *A. flavus* NRRL 30797 (target DNA) obtained by qPCR with SyBR Green as the fluorescent dye. Ct values are averages of three independent dilution series (A). Representative qPCR analysis (B) and dissociation curves (C) of soil samples receiving single Mater-Bi® (MB) and incubated for 30 and 60 days.

The dynamics of the soil *A. flavus* population was also studied using qPCR (FIG. 10). Correlation between Ct values obtained from soil DNA and size of viable propagules, estimated by plate counting, gave a determination coefficient <0.68 (data not shown). Low correlation can be due to a number of reasons. Efficiency of DNA recovery can depend on the initial total amount which is variable over time due to both cell growth and due to mycelia fragments existing as multinucleate structures (Gow and Gadd. 1995. *The Growing Fungus*, Chapman & Hall, London, UK). Additionally, qPCR does not discriminate DNA from viable and non-viable propagules (Mayer et al. 2003. *Int. J. Food Microbiol.* 82: 143-151); thus artificially high representations of dead propagules may result. In the experiment described here, data are consequently expressed in terms of target DNA as calculated using the standard curve. As indicated in Table 3, the amount of target DNA increased during the first month of incubation and remained relatively constant during the remaining incubation period, which is compatible with results obtained using the cultural method (FIG. 6). In contrast to plant count data, amount of target DNA isolated from samples containing single Pesta granules was unaffected by incubation time. This was likely due to presence of the clay fraction of Pesta granules which would reduce the efficiency of DNA recovery. As expected, total *A. flavus* DNA isolated from MB granules introduced in soil increased over the incubation period, thus confirming that the proposed starch-based material supported fungal growth. Soil samples receiving increasing dosage of MB granules showed similar amount of target DNA as estimated by qPCR.

TABLE 3

Total amount of *A. flavus* NRRL 30797 DNA (× $10^3$ fg/g) isolated from soil samples in different treatment groups.

| | Amount of target DNA Incubation time | | |
|---|---|---|---|
| Treatment# | 10 days | 30 days | 60 days |
| Soil + 1 Mater-Bi ® granule | 1.72 ± 0.31* | 20.12 ± 6.23 | 21.33 ± 3.99 |
| Soil + 2 Mater-Bi ® granules | 0.90 ± 0.29 | 17.56 ± 4.91 | 19.57 ± 4.28 |
| Soil + 3 Mater-Bi ® granules | 1.11 ± 0.35 | 19.30 ± 3.84 | 18.74 ± 2.98 |
| Soil + 1 Pesta granule | 25.32 ± 5.55 | 27.11 ± 6.01 | 24.96 ± 5.97 |

*Numbers are means of three replicates ± SE
#Incubated with varied numbers of granules at 25° C.

Example 10

Field Colonization of Soil by the *A. flavus* K49-Mater-Bi® Biocontrol Composition Two field trials were conducted at Elizabeth, Miss. in 2008, to compare the efficacy of formulations of the non-toxigenic *A. flavus* strain K49 in colonization efficacy and suppression of aflatoxin contamination. A randomized complete block design of three treatments replicated in four blocks was used. Each experimental unit consisted of two inoculated rows with an uninoculated buffer row on each side of the inoculated row. The corn was planted on Apr. 14, 2008, and inoculation treatments were implemented on July $10^{th}$ (ears already formed). Two experimental plots were used: the first, designated native (i.e., non-inoculated with F3W4 toxigenic fungi) received either wheat- or bioplastic-colonized non-toxigenic isolate K49 as a soil inoculant. The second field was inoculated with the wheat colonized by the toxigenic *A. flavus* strain F3W4 as described elsewhere (Abbas et al. 2006, supra) and treated with either wheat- or bioplastic-colonized non-toxigenic isolate K49 as a soil inoculant. The F3W4 wheat inoculant, the K49 bioplastic formulation and the K49 wheat formulation were applied at a rate of ~10 kg/ha.

Figure 11:
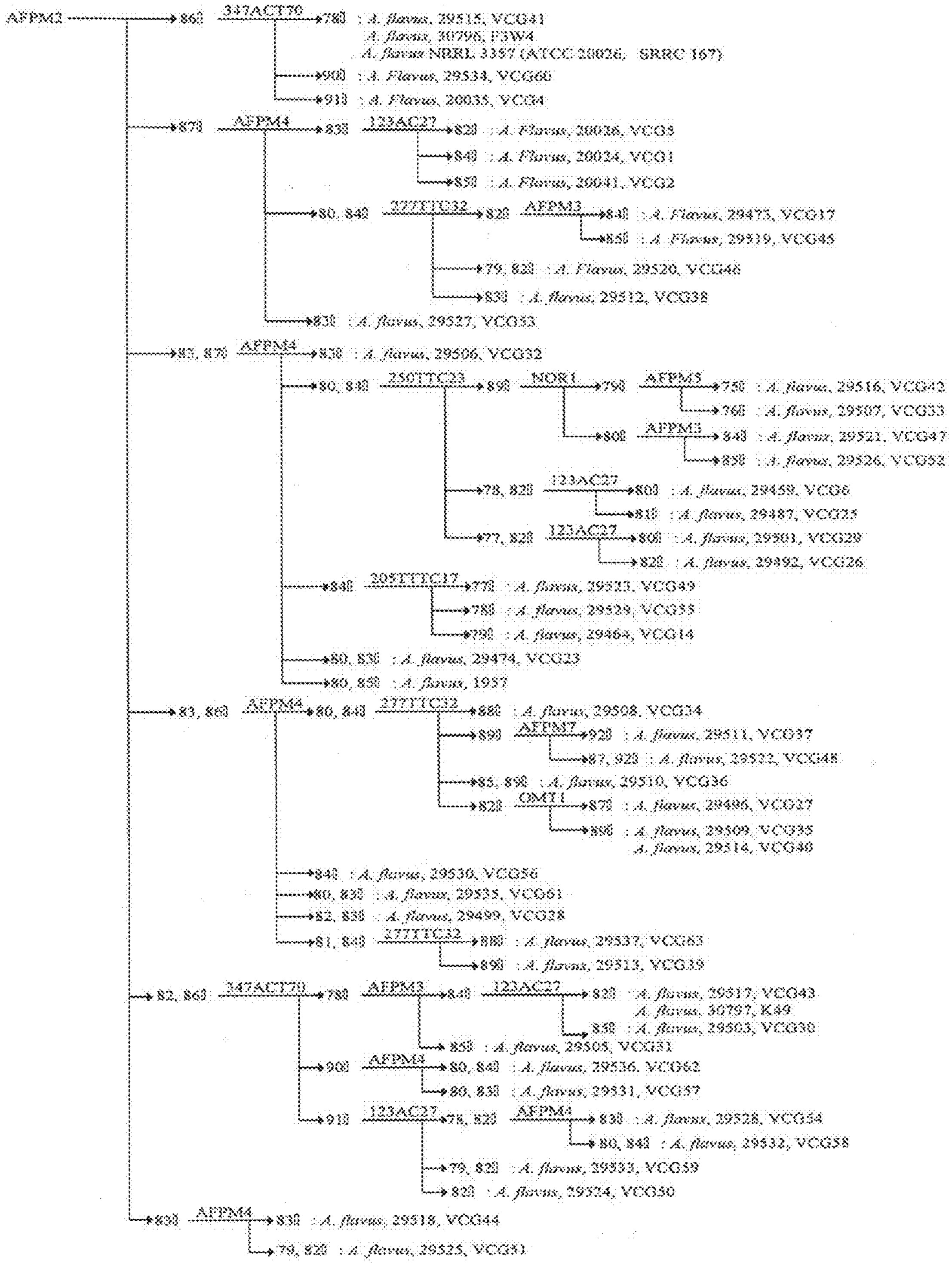
FIG. 11 depicts a flowchart for Tm based vegetative compatibility grouping of *Aspergillus flavus* strains.

Soil (0 to 2 cm) was sampled at the time of corn harvest and was plated on selective MDRB media using methods described in Abbas et al. (2006, supra). Forty colonies from each plot were assessed for aflatoxin production as determined by fluorescence on B-cyclodextrin PDA and colony pigmentation assays (Abbas et al. 2004, supra). Most of these typing methods require long cultivation periods and highly trained personnel. To reduce the labor and increase the ease and accessibility of identification, we have developed a fungal typing system which utilizes real time polymerase chain reaction (qRT-PCR) and melt curves (Tm) to genotype *Aspergillus* strains. Using this methodology, a fungal vegetative compatibility group (VCG) identification flowchart was generated using known Aspergilli strains (FIG. 11). The majority of the known strains were provided by Dr. Bruce Horn, USDA. The known strains represent the vegetative compatibility groups of *Aspergillus flavus* found in Georgia. Additional strains, i.e., *A. flavus* K49, *A. flavus* NRRL 3357 and *A. flavus* F3W4, strains of Abbas et al. were also used to construct the identification tree.

No effect of inoculation with either F3W4 or K49 on aflatoxin concentration in corn grain was observed as aflatoxin were less than 2 ppb. The inoculation was conducted fairly late in the season as ears were already forming; typically inoculation is done mid season at 10 leaf stage. In addition, the amount of rainfall later in corn ontogeny was not favorable for aflatoxin contamination.

The recovery of toxigenic *A. flavus* isolates are presented in Table 4. In native control soil that was not treated with F3W4, about 55% of the *A. flavus* recovered from soil in September and about 52%, recovered in November, were typed as aflatoxin producers based on the cultural techniques (fluorescence on β-cyclodextrin PDA and yellow pigmented colonies). Soil inoculated with K49 colonized wheat was not significantly different from the non-inoculated control on either date (37% and 40%, respectively); however, the *A. flavus* propagules recovered from soil inoculated with K49 colonized bioplastic was reduced to 23% in September and 17% in November. In soil that was inoculated with the toxigenic *A. flavus* strain F3W4, about 88% of the isolates recovered from control soils were toxigenic in both samples. When K49 was inoculated as a wheat inoculant, the distribution of toxigenic isolates was not affected. However when K49 was added as a Mater-Bi® inoculants, the recovery of toxigenic isolates was significantly reduced to 65.8% in September and 36% in November. These results indicate that the bioplastic material is a suitable matrix for inoculating soil to displace the toxigenic *A. flavus* population.

TABLE 4

Effect of inoculation with non-toxigenic isolate K49 as a wheat or bioplastic (MB) formulation on toxigenic properties of *A. flavus* recovered from surface soil.

| Treatment | Native | F3W4 |
|---|---|---|
| | Toxigenic Isolates (%) | |
| September (Corn Harvest) | | |
| Control [No K49] | 54.8 a | 87.5 a |
| K49 Wheat | 37.0 ab | 88.3 a |
| K49 Mater-Bi ® | 23.3 b | 65.8 b |
| November | | |
| Control [No K49] | 52 a | 88 a |
| K49 Wheat | 40 a | 70 a |
| K49 Mater-Bi ® | 17 b | 36 b |

Mean of four replicates for both experiments, means followed by the same letter do not differ at the 95% confidence level.

Using the Tm method and the identification flowchart (FIG. 11) *A. flavus* isolates of soil cultures from Elizabeth, Miss. were performed. A total of 89 samples were randomly selected and analyzed and Tm profiles were generated. Approximately 77% of these strains could be placed into one of the known VCGs. Of these identifiable strains 37% correspond to VCG41 which also contains the toxigenic *A. flavus* NRRL 3357 and F3W4. A total of 40.4% corresponded to VCG 43 group which contains the biocontrol strain K49 and the type strain of 29517 (FIG. 11). Comparing this VCG group to the pigment and UV test for aflatoxin, the number of presumptive K49 strains can be identified. Strains that were negative on both UV and pigment test are assumed to be K49, strains positive on both are presumed to be *A. flavus* 29517 like strains, and samples showing a combination of positive and negative test are assumed to be a mixture of the two. Using these parameters we find that in the non-inoculated control soils, 33% of the tested samples are related to K49, and in the K49 wheat inoculated treatments 36% are K49 like (Table 5). However of the isolates typed from the bioplastic treated soil 72% are K49-like. This genotyping methodology supports the observations deduced using cultural methods confirming the superiority of the bioplastic material to enhance the competitiveness of strain K49 in displacing native toxigenic isolates.

TABLE 5

Analysis of 89 *A. flavus* isolates from native (non-F3W4 inoculated) soil sampled in September.

| Treatment | Toxin Producer* | Isolates Tested | Isolates in K49 VCG | % Isolates in K49 VCG |
|---|---|---|---|---|
| Control | Yes | 11 | 2 | 18.2 |
| Control | No | 18 | 6 | 33.3 |
| K49 Wheat | Yes | 4 | 2 | 50.0 |
| K49 Wheat | No | 39 | 14 | 35.9 |
| Mater-Bi ® | Yes | 6 | 5 | 83.3 |
| Mater-Bi ® | No | 11 | 8 | 72.7 |

*Toxin production ascertained based on cultural methods.

Example 11

Biocontrol of Damping-Off of Impatiens Using a Biocontrol Composition Comprising Trichoderma virens-Inoculated Mater-Bi® Granules Granules of bioplastic Mater-Bi® were inoculated with spores of the isolate Gv29-8 of *Trichoderma virens* following the procedure described for *Aspergillus flavus K*49. The *T. virens* was cultured on acidified potato dextrose agar (PDA) for 10 days and conidia were harvested in 0.02% Tween 20 resulting in a suspension of log 8.9 propagules/mL. Mater-Bi® PE granules (800 g) were incubated with one liter of suspension and shaken for 4 hours, then dried at 40° C. for 2 hours.

To characterize patterns of Trichoderma colonization of the bioplastic matrix and soil mix, quantitative PCR (qPCR) was performed on a ABI Prism 7700 Sequence Detection System (Applied Biosystem) using *T. virens* specific primers (Hagn et al. 2007.). The reaction mixture (25-μL) consisted of: 2 μl, of DNA, 12.5 μl of 2× TaqMan Universal PCR Master Mix (Applied Biosystems, CA), and 7 pmol of each primer (Tf/uTr). Thermocycling conditions were as follows: 10 min at 95° C., and 35 cycles of 95° C. for 30 s, 55.5° C. for 30 s, and 72° C. for 30 s.

The efficacy of bioplastic-formulated Trichoderma as a biocontrol agent for damping-off caused by *Rhizoctonia solani* was assayed in greenhouse study. A sufficient mass of a potting mix was infested with *R. solani* NRRL 22805 using the method described in Honeycutt and Benson (2001. *Plant Disease* 85: 1241-1248), with minor changes. Briefly, four 3-mm agar plugs from actively growing cultures of NRRL 2205 were placed into 250-mL bottles containing barley grains (25 g of grains and 18 mL of water) that had been autoclaved three times for consecutive days. Bottles were incubated at 25° C. in the dark. Bottles with non-inoculated grains were included. After a 2-week incubation, grains were pulverized, passed through a 2-mm sieve and added to the potting mix at the ratio of 1 and 10% (w/w). Bioplastic granules were added to the differently prepared mixture at the ratio of 15 mg/g of potting mix. Before use, the mixtures were incubated for 4 days at 25° C. and finally used for filling seedling trays. Trays were planted with impatiens (*Impatiens wallerana*) and incubated in a growth chamber at 25° C. supplemented with light for 12-h period. A total of 200 seeds were planted for single treatment. The experiment was arranged in a completely randomized block design and the plant stand was monitored for 2 weeks.

The survival of and colonization of the soil mix by introduced *T. virens* was assessed by quantifying target DNA by real-time PCR using methods described above. Total DNA from the potting mixture was isolated using the commercial kit PowerSoil (MoBio Laboratories Inc.) following the instructions of the manufacturer. For each plot, triplicate samples of DNA extracts were pooled, concentrated by vacuum and resuspended in TE buffer.

Mater-Bi® PE granules treated in this manner produced a formulation log 7.2 propagules/granule. Storage of *T. virens* granules at 25° C. for 90 d maintained >90% of initial propagule density. The quantification of target *T. virens* DNA by real-time PCR showed that the bioplastic matrix can support the fungal growth. More precisely, the amount of target DNA recovered from inoculated granules was 371 and 1321 ng/g granule at the beginning and after 10 days of the incubation. These data support cultural methods that demonstrate that the bioplastic granules can provide a satisfactory matrix for colonization by the biocontrol fungus *T. virens.*

Figure 12:
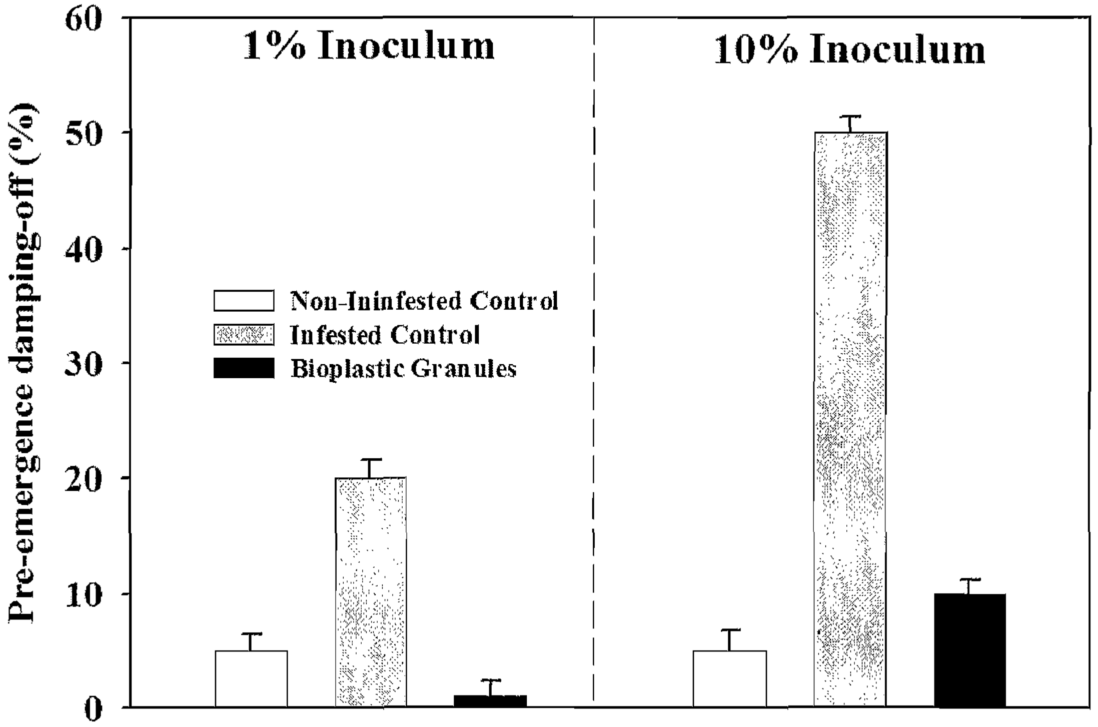
FIG. 12 depicts the influence of bioplastic granules inoculated with the biocontrol fungus *Trichoderma virens* on damping-off of impatiens caused by *Rhizoctonia solani*. Seeds of impatiens were planted in a potting mix amended with 1% and 10% (w/w) of grain seeds inoculated with *R. solani*. Each bar represents mean±STD (n=200).

As shown in FIG. 12, pre-emergence damping-off of impatiens seedlings was of 20% and 50% in potting mix amended with 1% and 10% of *R. solani* inoculum, respectively. In both cases, presence of bioplastic granules inoculated with the biocontrol fungus *T. virens* Gv29-8 significantly reduced damping-off of seedlings. When soil mix was treated with 1% *Rhizoctonia* there was a 90% reduction in disease incidence when inoculated with Bioplastic formulated *T. virens* compared to the no Trichoderma control. The level of *Rhizoctonia* incidence increased by almost 250% when the Rhizoctonia density was increased to 10%, with subsequent disease suppression equal to ~80% when treated with *Trichoderma* in bioplastic. As presented in Table 6, propagules of *T. virens* increased by thirty-fold from 5 to fifteen days after the initiation of the greenhouse study. This colonization data supports the efficacy of damping-off biocontrol obtained using the bioplastic formulated fungus and that soil treated with the bioplastic formulation is subject to a rapid colonization by *T. virens*.

TABLE 6

Total amount of *T. virens* * DNA and propagules isolated# from potting mix.

| Time (Days) | Amount of target DNA (ng/g) | Propagules (× $10^3$ cfu/g) |
|---|---|---|
| 5 | 0.66 ± 0.21 | 1.22 ± 0.50 |
| 10 | 19.01 ± 0.33 | 21.13 ± 0.59 |
| 14 | 26.23 ± 0.49 | 38.31 ± 11.2 |

**T. vixens* Gv29-8

#Isolated from potting mix incubated at 25° C. after having received 1% (w/w) of grain seeds inoculated with *R. solani* and bioplastic granules (15 mg/g of potting mix).

Example 12

Biocontrol of *A. flavus* in Corn Using Bioplastic Granules Inoculated with the *A. flavus* Non-aflatoxigenic Strain NRRL 30797

A field trial was conducted in a commercial corn field located at the experimental farm of the University of Bologna (Cadriano, Bologna) using Mater-Bi® PE granules. Bioplastic granules were inoculated with the non-aflatoxigenic strain *A. flavus* NRRL30797, following the procedure described in Accinelli et al. (2009. *Bioresource Tech.* 100:3997-4004). The final potency of the granules was of log 7.4 cfu/granule. A randomized, complete block design of three treatments replicated in three blocks was used. Experimental treatments were: A) untreated control; B) NRRL 70797-inoculated granules at a rate of 20 kg/ha; C) NRRL 70797-inoculated granules at a rate of 30 kg/ha. Each replicate/plot consisted of a 600 m2 (20 m×30 m) area surrounded by a 15-m wide buffer zone. A conventional corn hybrid (Pioneer Hi-Bred PR31K18) was planted on Apr. 16, 2009 and managed according to ordinary practices of the region, which include two irrigations. Bioplastic granules were manually applied on May 28, 2009.

Corn was harvested on Aug. 25, 2009. A total of 60 corn ears were randomly collected from each plot and processed for chemical analysis and for assessing the percentage of kernels that were colonized by *A. flavus* and the corresponding frequency of aflatoxigenic isolates. For aflatoxin analysis, a total of 50 ears per plot were shelled, dried at 35° C. for 48 hours and finally ground at 1 mm. Aflatoxin analyses were performed by the ISO (International Standardization Office) 9001 Certified Laboratory of the Chamber of Commerce, Bologna, Italy following MIP AGER (Mycotoxin Program, Association of Cereal Growers of Emilia Romagna) GLP procedures (AFLA rev. 7 2008) (detection limit: 0.5 ng g−1). Remaining ears were used for microbiological analysis adopting the procedure described in Abbas et al. (2004b, supra), with minor modifications. Briefly, kernels were surface sterilized in 0.3% sodium hypochlorite solution for 2 min and rinsed three times in sterile distilled water. After drying 1 hour under a laminar hood, grains were plated on MDRB agar and incubated at 38° C. After 5 days of incubation, the percentage of kernels infected by *A. flavus* colonies was recorded. A number of *A. flavus* isolates (20 isolates for plot) were picked, and their potential to produce aflatoxin B1 (AFLB1) was evaluated. Single isolates were cultured in 2 mL of yeast extract sucrose at 25° C. After 7 days of incubation, 2 mL of chloroform were added to each tube. Tubes were vortexed for 2 min and left standing for 5 min. The chloroform layer was then transferred to centrifuge tubes, dried under vacuum and samples were redissolved in water/ethanol (30/70). The concentration of aflatoxin B1 was measured by HPLC as described in Abbas et al. (2004b, supra). Data were expressed as total mass of aflatoxin B1 per gram of biomass, after drying at 80° C. overnight. Data were subjected to analysis of variance (ANOVA) using the software package Statistica 8.0 (StatSoft Inc.; Tulsa, Okla.).

Concentrations of AFLB1 in corn samples are reported in Table 7. The level of AFLB1 in untreated control was generally low, not exceeding 5.2 ng g−1. The weather conditions were not conducive for aflatoxin contaminations in this particular year; however, application of bioplastic granules inoculated with the aflatoxigenic isolate NRRL 30797 lead to a significant decrease of AFLB1 concentration in corn grains (Table 7). Results of this field experiment showed that the highest dosage (30 kg/ha) was the most effective in reducing aflatoxin contamination of corn grains. These results are consistent with those of the microbiological analysis. Approximately 87% of the grains from the untreated control were contaminated with aflatoxigenic isolates. The relative abundance of aflatoxigenic strains was lower in grains of treated plots. Approximately half of the total *A. flavus* strains isolated from grains of treated plots had the potential to produce AFLB1. Strains isolated from plots receiving the highest application rate, showed the lowest average ability to produce AFLB1 per grams of mycelium. Our data confirmed that this technology was effective in the replacement of naturally occurring aflatoxigenic isolates and finally to reduce AFLB1 in corn.

TABLE 7

Effect of application rate of inoculated bioplastic granules on aflatoxin B1 concentrations of corn kernels, and relative abundance of aflatoxigenic isolates recovered from corn kernels and corresponding potential to produce aflatoxin B1.

| Application rate ($kg\ ha^{-1}$) | AFB1 conc. in ground kernels ($ng\ g^{-1}$) | Aflatoxigenic isolates (%) | Aflatoxin production (ng g − 1 dried *mycelium*) |
|---|---|---|---|
| Untreated Control | 4.1 ± 0.9 | 100 | 41.8 ± 8.1 |
| 20 | 1.8 ± 0.4 | 43 | 21.8 ± 6.7 |
| 30 | 0.6 ± 0.1 | 50 | 7.0 ± 2.9 |

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A biocontrol composition consisting essentially of an isolated *Aspergillus flavus*, strain NRRL 30797, and a bioplastic granule.

2. A method of reducing aflatoxin contamination of corn consisting essentially of administering the composition of claim 1 to the corn.

* * * * *